US012440631B1

(12) United States Patent
Jiang

(10) Patent No.: US 12,440,631 B1
(45) Date of Patent: Oct. 14, 2025

(54) ELECTRIC SUCTION DEVICE FOR EMERGENCY AIRWAY OBSTRUCTION REMOVAL

(71) Applicant: Handong Jiang, Yueqing (CN)

(72) Inventor: Handong Jiang, Yueqing (CN)

(73) Assignee: Handong Jiang, Yueqing (CN)

( * ) Notice: Subject to any disclaimer, the term of this patent is extended or adjusted under 35 U.S.C. 154(b) by 0 days.

(21) Appl. No.: 18/827,692

(22) Filed: Sep. 7, 2024

(51) Int. Cl.
*A61M 16/00* (2006.01)
*A61B 17/24* (2006.01)
(Continued)

(52) U.S. Cl.
CPC ......... *A61M 16/0009* (2014.02); *A61B 17/24* (2013.01); *A61B 17/50* (2013.01);
(Continued)

(58) Field of Classification Search
CPC ......... A62B 18/025; A62B 18/02–084; A61M 16/06–0655; A61M 2016/0661; A61M 2210/0625; A61M 1/64; A61M 1/65; A61M 1/67–684; A61M 1/71; A61M 1/80–82; A61M 2202/0014; A61M 16/0605;
(Continued)

(56) References Cited

U.S. PATENT DOCUMENTS 10,052,115 B2 8/2018 Lih
11,478,575 B1 10/2022 He
(Continued)

FOREIGN PATENT DOCUMENTS

WO WO-2009017272 A1 * 2/2009 .......... A61M 1/0003

OTHER PUBLICATIONS

Translation of WO_2009017272_A1 (Year: 2009).*
(Continued)

*Primary Examiner* — Kendra D Carter
*Assistant Examiner* — Mautin I Ashimiu
(74) *Attorney, Agent, or Firm* — PORUS IP LLC

(57) ABSTRACT

Disclosed herein are embodiments of an electric suction device for emergency airway obstruction removal and anti-choking, relating to the field of emergency rescue technology. One embodiment comprises a face mask, with an electric suction mechanism set on the surface of the face mask. The electric suction mechanism includes an oral support that is movably installed inside the face mask. The face mask is pressed tightly against the face and adjusted to form a sealed space. Activating the electric suction mechanism switch triggers the control circuit board to power the one-way suction module via the battery. This controls the one-way suction module to extract air, creating negative pressure in the sealed space.
Consequently, the obstructing object is suctioned out of the airway due to continuous negative pressure. When the patient is unconscious or unable to cooperate, the oral support can be inserted into the patient's mouth to ensure that the patient's mouth is open and the device can be used. This device is easy to operate, safe and stable. The suction of this device can be controlled and there are different types of masks that can be configured to meet different people. It can be used independently by the patient without third-party assistance, or by a rescuer when the patient is unable to perform self-rescue.

7 Claims, 5 Drawing Sheets

(51) Int. Cl.
*A61B 17/50* (2006.01)
*A61M 16/04* (2006.01)
*A61M 16/06* (2006.01)

(52) U.S. Cl.
CPC .... *A61M 16/0057* (2013.01); *A61M 16/0488* (2013.01); *A61M 16/0605* (2014.02); *A61M 2202/0014* (2013.01); *A61M 2202/06* (2013.01); *A61M 2205/8206* (2013.01); *A61M 2205/8237* (2013.01); *A61M 2209/088* (2013.01); *A61M 2210/0625* (2013.01)

(58) Field of Classification Search
CPC .......... A61M 16/0683; A61M 16/0009; A61M 16/0488; A61M 16/049; A61M 16/0493; A61B 17/50; A61B 2217/005; A61B 17/24; A41D 13/1161
See application file for complete search history.

(56) References Cited

U.S. PATENT DOCUMENTS

| | | | | |
|---|---|---|---|---|
| D996,602 | S | 8/2023 | Jiang | |
| 2015/0290415 | A1* | 10/2015 | Dunn | A61M 16/0616 128/205.25 |
| 2019/0175202 | A1* | 6/2019 | Piatyszek | A61M 1/80 |
| 2024/0066242 | A1* | 2/2024 | Lv | A61B 17/50 |

OTHER PUBLICATIONS

"Automatic Choking Rescue Device, Anti Choking Device with 3 Inflatable Masks, Electric Airway Suction Device for Self Rescue, Choking Device for Kids and Adults, Choking First Aid Device", Web page <https://www.amazon.com/gp/product/B0CZP5XFXR>, Apr. 2, 2024.

* cited by examiner

ELECTRIC SUCTION DEVICE FOR EMERGENCY AIRWAY OBSTRUCTION REMOVAL

TECHNICAL FIELD

Disclosed herein are embodiments of an electric suction device for emergency airway obstruction removal, relating to the field of emergency rescue technology.

BACKGROUND ART

Human life activities require oxygen, which enters the body through the airway, while metabolic waste gas-carbon dioxide-is also expelled through the airway. The airway, also known as the respiratory tract, is an important duct system that provides gas exchange for our body and is our life passage. This passage must remain unobstructed at all times for normal life activities to be maintained.

According to relevant data, approximately 13,5000 people worldwide die from suffocation each year, with children under five accounting for 17%. For the elderly, due to physical deterioration, drug side effects, and dentures, the risk of death from suffocation increases with age starting from 71 years old. This risk is often exacerbated by living alone or wearing dentures.

Patent publication number U.S. Pat. No. 10,052,115B2 disclosed a choking intervention device for clearing an object obstructing a breathing passage of a choking victim, the device comprising: a bellows, a handle provided on the bellows; a facemask coupled to the base of the bellows.

To address the problem of foreign objects blocking the airway and affecting breathing, existing technology utilizes an air cushion mask to create negative pressure in the airway. However, this still requires a third party to provide significant upper body strength to provide external force, which is uncontrollable and may cause damage to the patient's lungs, facial bones, and muscles.

SUMMARY OF THE INVENTION

The purpose of the present invention is to provide an electric suction device for emergency airway obstruction removal to address the issues raised in the background.

To solve the above technical problems, the invention adopts the following technical solution:

One embodiment of an electric suction device for emergency airway obstruction removal comprises a face mask; an electric suction mechanism equipped on the surface of the face mask; and a wearing connection mechanism equipped on the surface of the electric suction mechanism.

The electric suction mechanism includes an oral support movably installed inside the face mask; a shell movably installed at the bottom end of the oral support, with exhaust holes evenly distributed at the bottom end of the shell; and a suction tube connectively installed at one end of the oral support and inside the shell.

Further improvements of the invention's technical solution include: the electric suction mechanism also includes a battery, which is fixedly installed inside the shell. A control circuit board is fixedly installed at the bottom end of the battery, and a charging interface is fixedly installed on the surface of the control circuit board.

Further improvements of the invention's technical solution include: the charging interface extends to the surface of the shell. A button transmission component is movably installed on the surface of the charging interface. A press switch is fixedly installed at the bottom end of the button transmission component, and the press switch is movably installed on the surface of the shell.

Further improvements of the invention's technical solution include: the wearing connection mechanism includes a casing, which is fixedly installed on the surface of the shell. There are two sets of casings, which are stacked and distributed on the surface of the shell. A retractable band is movably connected to the surface of the casing. The surface of the retractable band is fixedly installed with hook-and-loop fasteners.

Further improvements of the invention's technical solution include: the wearing connection mechanism also includes a support column, which is movably installed inside the casing. A rotating disk is movably installed on the surface of the support column, and a mainspring is fixedly installed on the surface of the support column.

Further improvements of the invention's technical solution include: one end of the mainspring is fixedly installed with a fixed column, which is fixedly installed on the surface of the rotating disk. The fixed column is fixedly installed on the surface of the retractable band. The surface of the retractable band is movably connected with a stopper rod, which is fixedly installed inside the casing. One end of the retractable band is fixedly installed with a limit rod.

Further improvements of the invention's technical solution include: a one-way suction module is set on the surface of the control circuit board, and the one-way suction module is fixedly installed inside the shell. The top end of the one-way suction module is adapted to the suction tube.

Compared to the existing technology, the technical advancements achieved by adopting the aforementioned technical solution in this invention are as follows:

1. This invention provides an electric suction device for emergency airway obstruction removal. By using the oral support, suction tube, one-way suction module, shell, charging interface, press switch, exhaust holes, button transmission component, control circuit board, and battery in coordination, the face mask is placed on the patient's mouth and nose and adjusted to form a sealed space. The battery supplies power to the control circuit board and one-way suction module. Pressing the press switch causes the button transmission component to open the control circuit board inside the shell. At this time, the control circuit board triggers the battery to power the one-way suction module, controlling the one-way suction module to create a suction effect. The face mask 1 is placed over the patient's mouth and nose and adjusted to form a sealed space. The battery 210 supplies power to the control circuit board 209 and the one-way suction module 203. When the press switch 206 is pressed, it pushes the button transmission component 208 to activate the control circuit board 209 inside the shell 204. At this point, the control circuit board 209 triggers the battery 210 to power the one-way suction module 203, controlling it to suction outward unidirectionally. Due to the constant negative pressure, objects in the patient's mouth are sucked out of the airway, while air is expelled through the exhaust holes 207.

If suction is unsuccessful, try again after a second or more times, and it can work. When the patient is unconscious or unable to cooperate, In cases where the patient is unable to cooperate, one end of the oral support (201) can be securely affixed within the mask and connected to the electric suction mechanism 2, while the other end is inserted into the patient's mouth. The mouth is supported and forms a channel with the airway. When the electric suction mechanism 2 is not in use, the battery 210 can be charged by connecting a charger to the charging interface 205. Additionally, different sizes of masks are used to fit different people to improve the adaptability of the device.

2. This invention provides an electric suction device for emergency airway obstruction removal. By using the casing, retractable band, hook-and-loop fasteners, rotating disk, fixed column, support column, mainspring, limit rod, and stopper rod in coordination, the retractable band drives the rotating disk to rotate inside the casing. The rotating disk, in turn, compresses the mainspring in conjunction with the fixed column and support column. The hook-and-loop fasteners on both sides of the retractable band are connected and fixed to the patient's head. After use, releasing the retractable band allows the mainspring to rebound, driving the rotating disk to retract the band. At this time, the stopper rod clamps the retractable band to prevent it from tangling during retraction. When the limit rod reaches the surface of the casing, the retractable band resets. This device ensures that even if the rescue personnel briefly release their hands while using the electric suction mechanism, the device will not easily move, thereby better assisting the rescue personnel in saving the patient and enhancing the device's adaptability.

Figure 1:
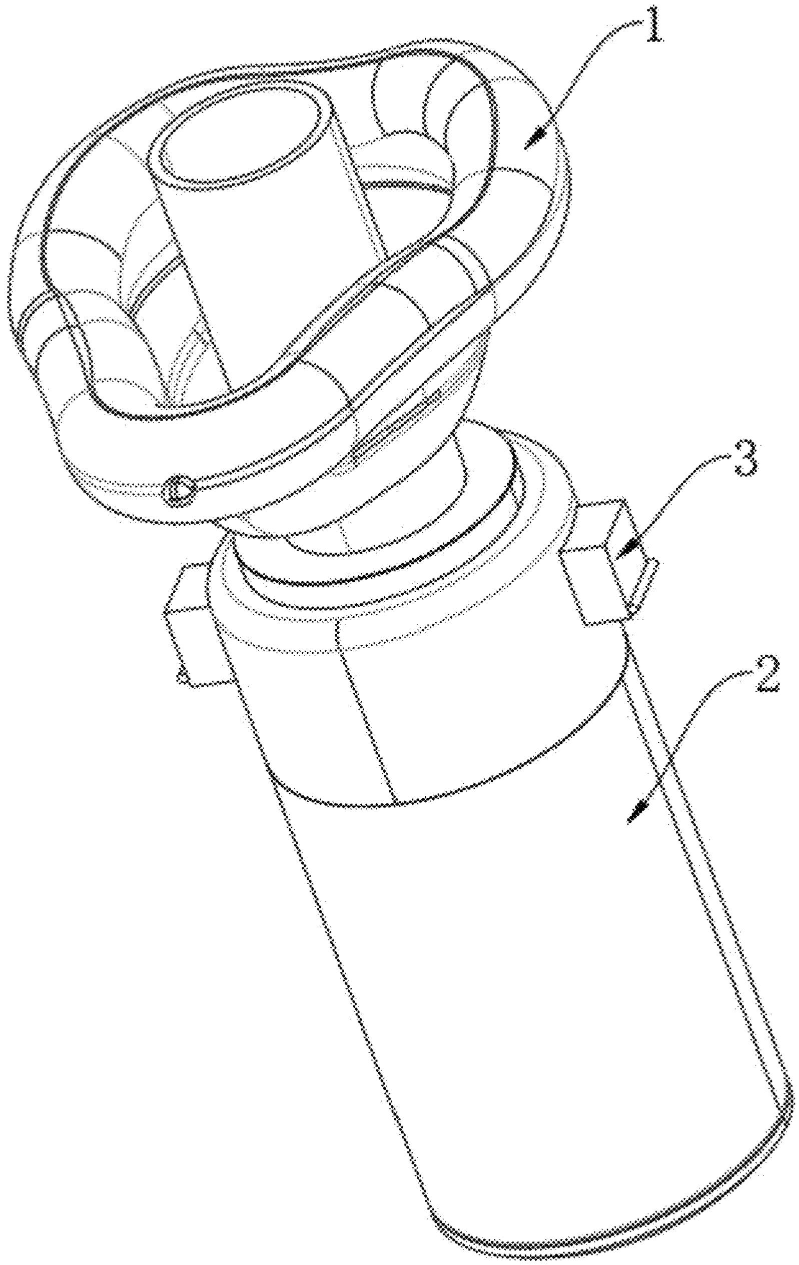
FIG. 1 is a perspective structural diagram of the invention.

Reference numerals in the figures: 1. Face mask; 2. Electric suction mechanism; 201. Oral support; 202. Suction tube; 203. One-way suction module; 204. Shell; 205. Charging interface; 206. Press switch; 207. Exhaust holes; 208. Button transmission component; 209. Control circuit board; 210. Battery; 3. Wearing connection mechanism; 301. Casing; 302. Retractable band; 303. Hook-and-loop fasteners (loop side); 304. Hook-and-loop fasteners (hook side); 305. Rotating disk; 306. Fixed column; 307. Support column; 308. Mainspring; 309. Limit rod; 310. Stopper rod.

DETAILED DESCRIPTION OF PREFERRED EMBODIMENTS

The following provides a further detailed description of the invention in conjunction with the embodiments:

Embodiment 1

Figure 2:
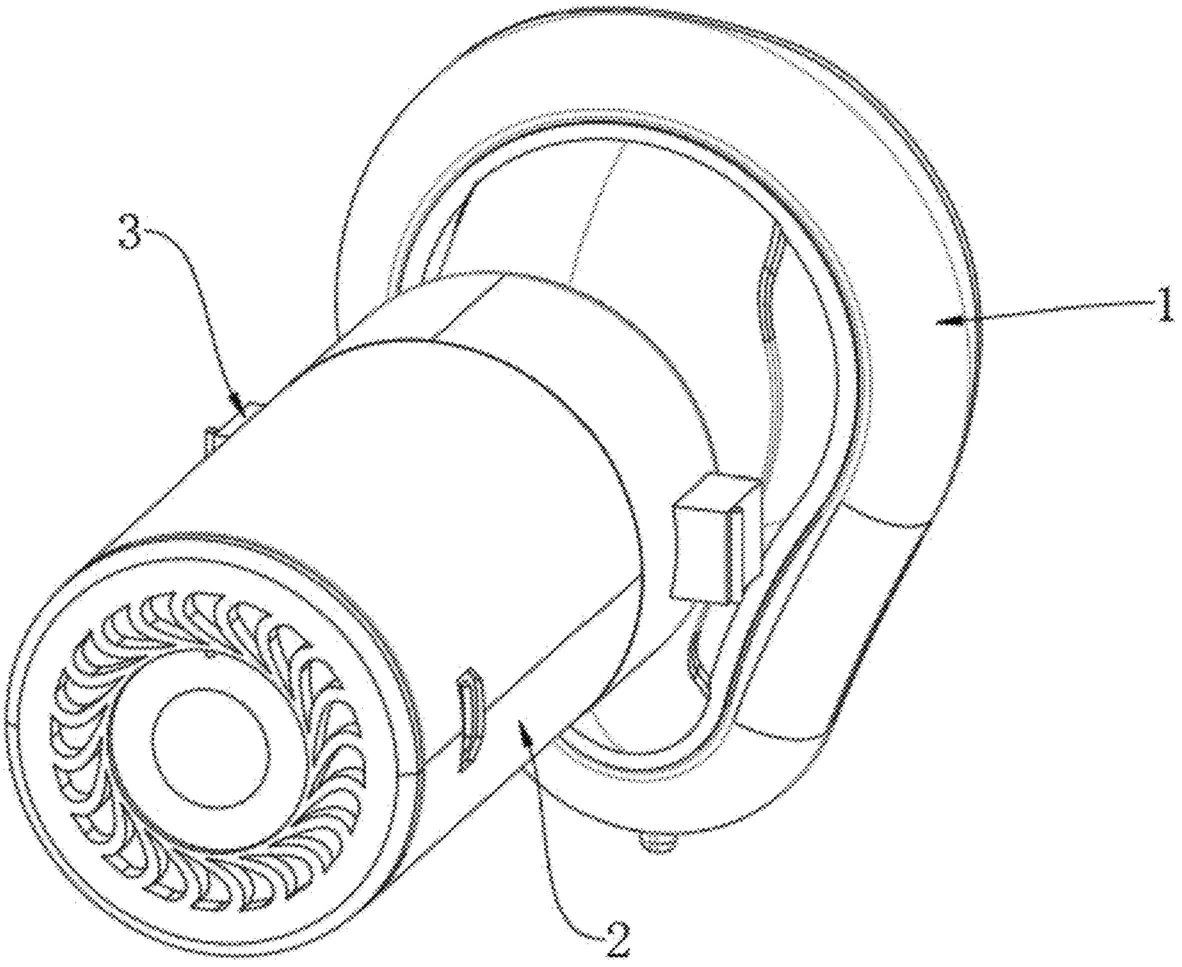
FIG. 2 is a structural diagram of an axial view of the invention.
Figure 3:
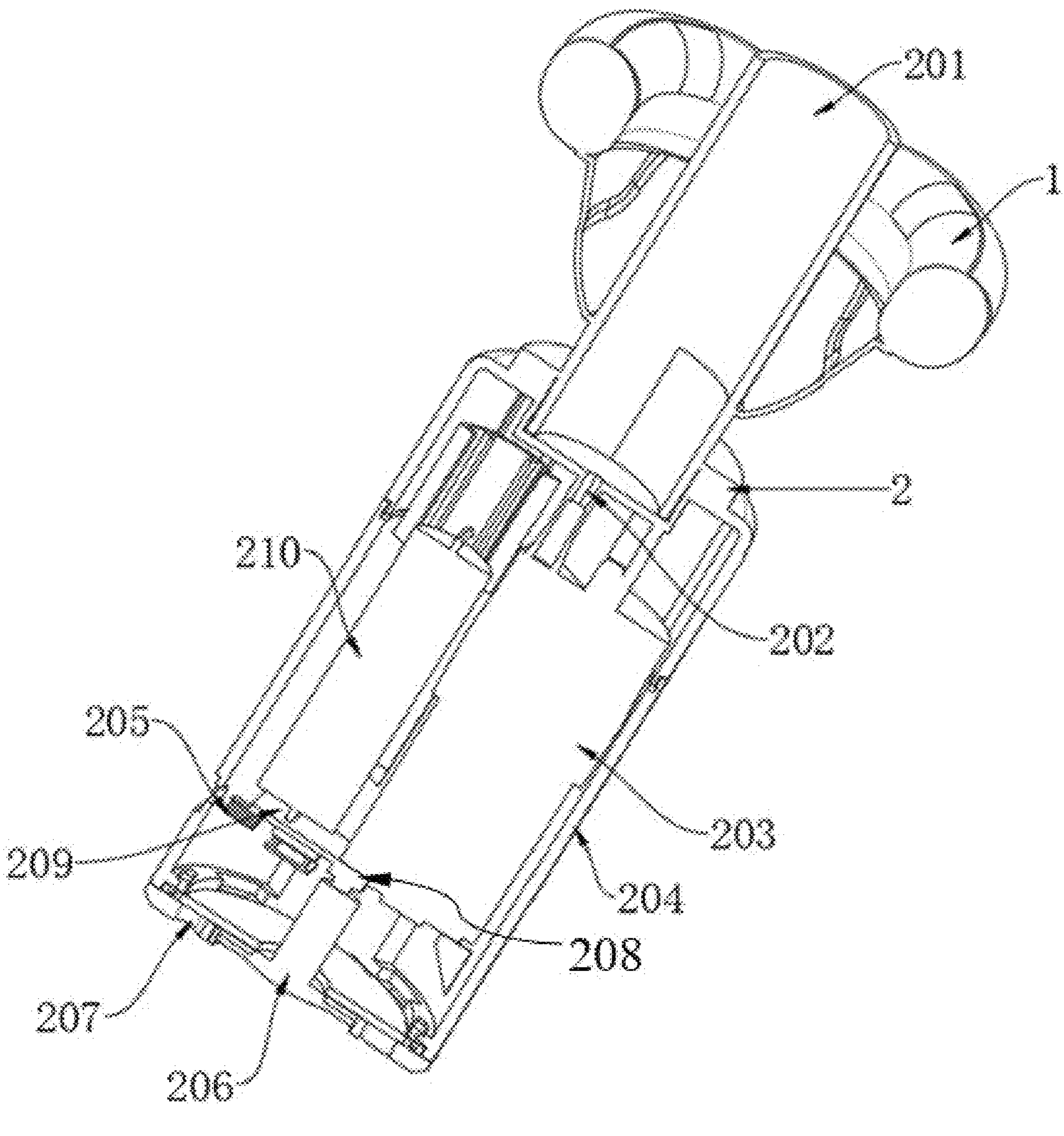
FIG. 3 is a sectional structural diagram of the electric suction mechanism of the invention.
Figure 4:
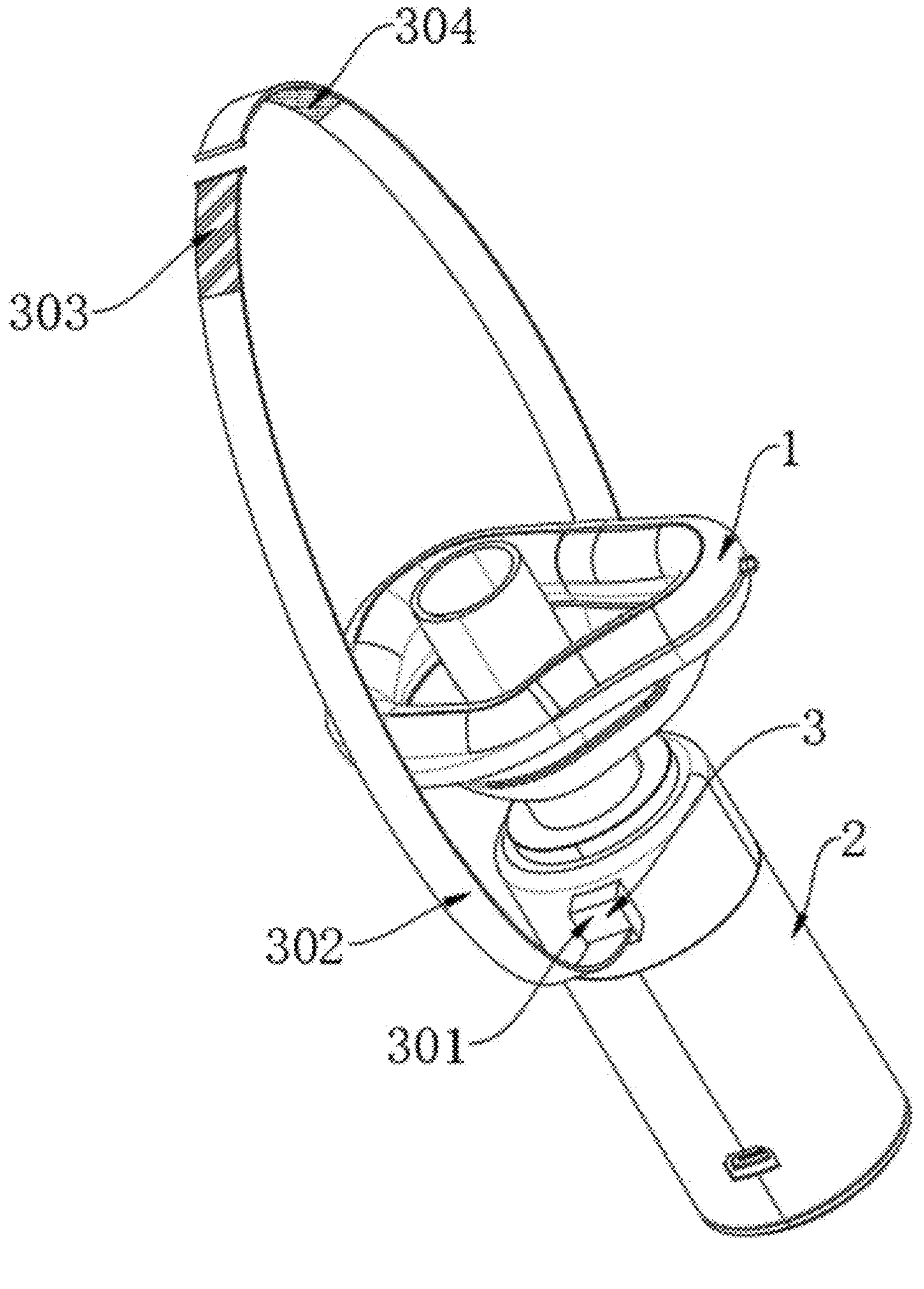
FIG. 4 is a structural diagram of the retractable band of the invention.
Figure 5:
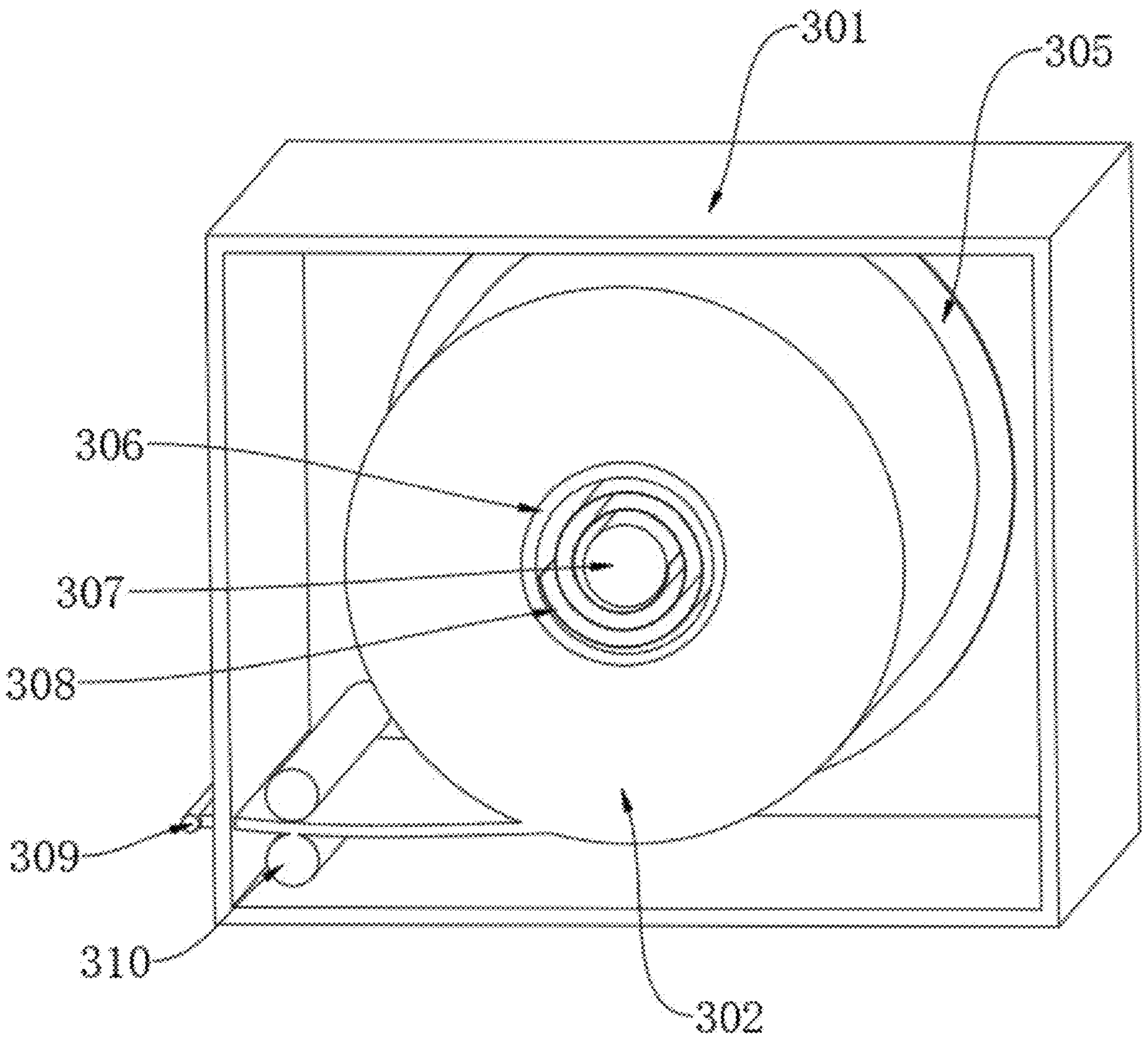
FIG. 5 is a structural diagram of the one-way suction module of the invention.

As shown in FIGS. 1-5, this invention provides an electric suction device for emergency airway obstruction removal, comprising a face mask 1, with an electric suction mechanism 2 installed on the surface of the face mask 1, and a wearing connection mechanism 3 set on the surface of the electric suction mechanism 2. The electric suction mechanism 2 includes an oral support 201, which is movably installed inside the face mask 1. A shell 204 is movably installed at the bottom end of the oral support 201, with exhaust holes 207 evenly distributed on the bottom of the shell 204. A suction tube (202) is fixedly installed within the electric suction mechanism 2. One end of the tube is exposed outside the shell 204 to facilitate assembly with the movable face mask 1, while the other end extends into the interior of the shell (204). The electric suction mechanism 2 also includes a battery 210 fixedly installed inside the shell 204. A control circuit board 209 is fixedly installed at the bottom of the battery 210. A charging interface 205 is fixedly installed on the surface of the control circuit board 209 and extends to the surface of the shell 204. A button transmission component 208 is movably installed on the surface of the charging interface 205, with a press switch 206 fixedly installed at the bottom of the button transmission component 208. The press switch 206 is movably installed on the surface of the shell 204. A one-way suction module 203 is set on the surface of the control circuit board 209 and fixedly installed inside the shell 204, with its top end compatible with the suction tube 202.

In this embodiment, the face mask 1 is placed over the patient's mouth and nose and adjusted to form a sealed space. The battery 210 supplies power to the control circuit board 209 and the one-way suction module 203. When the press switch 206 is pressed, it pushes the button transmission component 208 to activate the control circuit board 209 inside the shell 204. At this point, the control circuit board 209 triggers the battery 210 to power the one-way suction module 203, controlling it to suction outward unidirectionally. Due to the constant negative pressure, objects in the patient's mouth are sucked out of the airway, while air is expelled through the exhaust holes 207. If suction is unsuccessful, try again after a second or more times, and it can work. One end of the oral support (201) can be securely affixed within the mask and connected to the electric suction mechanism 2, while the other end is inserted into the patient's mouth. The oral support effectively separates the patient's teeth, thereby maintaining an open mouth without penetrating deeply into the throat, thus ensuring safety. The mouth is supported and forms a channel with the airway. When the electric suction mechanism 2 is not in use, the battery 210 can be charged by connecting a charger to the charging interface 205. Additionally, different sizes of masks are used to fit different people to improve the adaptability of the device.

Embodiment 2

As shown in FIGS. 1-5, based on Embodiment 1, this invention provides a technical solution: preferably, the wearing connection mechanism 3 includes a casing 301 fixedly installed on the surface of the shell 204. There are two sets of casings 301 distributed on the surface of the shell 204. A retractable band 302 is movably connected to the surface of the casing 301. Hook-and-loop fasteners (loop side) 303 are fixedly installed on the surface of the retractable band 302, and hook-and-loop fasteners (hook side) 304 are also fixedly installed on the surface of the retractable band 302. The wearing connection mechanism 3 also includes a support column 307 movably installed inside the casing 301. A rotating disk 305 is movably installed on the surface of the support column 307. A mainspring 308 is fixedly installed on the surface of the support column 307, with one end of the mainspring 308 fixedly installed on a fixed column 306. The fixed column 306 is fixedly installed on the surface of the rotating disk 305 and on the surface of the retractable band 302. A stopper rod 310 is movably connected to the surface of the retractable band 302 and fixedly installed inside the casing 301. A limit rod 309 is fixedly installed at one end of the retractable band 302.

In this embodiment, when the retractable band 302 is stretched, it drives the rotating disk 305 to rotate inside the casing 301. The rotation of the rotating disk 305 drives the mainspring 308, while the fixed column 306 and support column 307 work together to compress the mainspring 308. The hook-and-loop fasteners (loop side) 303 and hook-and-loop fasteners (hook side) 304 on both sides of the retractable band 302 are connected and fixed to the patient's head. When use is completed, the retractable band 302 is released, and the mainspring 308 recoils, driving the rotating disk 305 to rotate and retract the retractable band 302. At this time, the stopper rod 310 clamps the retractable band 302 to prevent it from tangling while retracting. When the limit rod 309 reaches the surface of the casing 301, the retractable band 302 is reset. This device can remain stable even if the rescue personnel briefly let go during the use of the electric suction mechanism 2, better assisting rescue personnel in saving patients and improving the device's adaptability.

The following specifically explains the working principle of this electric suction device for emergency airway obstruction removal.

As shown in FIGS. 1-5, this invention provides an electric suction device for emergency airway obstruction removal, comprising a face mask 1, with an electric suction mechanism 2 installed on the surface of the face mask 1, and a wearing connection mechanism 3 set on the surface of the electric suction mechanism 2. The electric suction mechanism 2 includes an oral support 201, which is movably installed inside the face mask 1. A shell 204 is movably installed at the bottom end of the oral support 201, with exhaust holes 207 evenly distributed on the bottom of the shell 204. A suction tube (202) is fixed inside the electric suction mechanism (2).

One section is inside the interior of shell (204), and the other extends to the outside of the electric suction mechanism (2). The suction tube will be attached with mask when oral support is not installed. The electric suction mechanism 2 also includes a battery 210 fixedly installed inside the shell 204. A control circuit board 209 is fixedly installed at the bottom of the battery 210. A charging interface 205 is fixedly installed on the surface of the control circuit board 209 and extends to the surface of the shell 204. A button transmission component 208 is movably installed on the surface of the charging interface 205, with a press switch 206 fixedly installed at the bottom of the button transmission component 208. The press switch 206 is movably installed on the surface of the shell 204. A one-way suction module 203 is set on the surface of the control circuit board 209 and fixedly installed inside the shell 204, with its top end compatible with the suction tube 202. In this embodiment, the face mask 1 is placed over the patient's mouth and nose and adjusted to form a sealed space. The battery 210 supplies power to the control circuit board 209 and the one-way suction module 203. When the press switch 206 is pressed, it pushes the button transmission component 208 to activate the control circuit board 209 inside the shell 204. At this point, the control circuit board 209 triggers the battery 210 to power the one-way suction module 203, controlling it to suction outward unidirectionally. Due to the constant negative pressure, objects in the patient's mouth are sucked out of the airway, while air is expelled through the exhaust holes 207. If suction is unsuccessful, try again after a second or more times, and it can work. When the patient is unconscious or unable to cooperate, The mouth is supported and forms a channel with the airway. When the electric suction mechanism 2 is not in use, the battery 210 can be charged by connecting a charger to the charging interface 205. Additionally, different sizes of masks are used to fit different people to improve the adaptability of the device.

The above provides a detailed description of this invention in general terms. However, based on this invention, some modifications or improvements can be made, which would be obvious to those skilled in the art. Therefore, any modifications or improvements that do not deviate from the spirit of this invention are within the protection scope of this invention.

The invention claimed is:

1. A device for emergency airway obstruction removal, comprising: a face mask (1); an electric suction mechanism (2) carried by the face mask (1);

the electric suction mechanism (2) comprising:

an oral support (201) movably installed inside the face mask (1);

a shell (204) movably installed at a bottom end of the oral support (201);

a plurality of exhaust holes (207) evenly distributed at a bottom end of the shell (204);

a suction tube (202) connectively installed at one end of the oral support (201) and inside the shell (204), wherein the oral support (201) is configured to separate a patient's teeth to maintain an open mouth without penetrating into a throat of the patient; and a wearing connection mechanism (3) equipped on a surface of the electric suction mechanism (2), the wearing connection mechanism (3) including two casings (301) stacked and distributed on a surface of the shell (204); and a retractable band (302) movably connected to a surface of one of the two casings (301), a surface of the retractable band (302) being fixedly installed with hook-and-loop fasteners.

2. The device of claim 1, wherein the electric suction mechanism (2) further comprises: a battery (210) fixedly installed inside the shell (204); a control circuit board (209) fixedly installed at a bottom end of the battery (210); and a charging interface (205) fixedly installed on a surface of the control circuit board (209).

3. The device of claim 2, wherein:

the charging interface (205) extends to a surface of the shell (204);

a button transmission component (208) is movably installed on a surface of the charging interface (205); and a press switch (206) is fixedly installed at a bottom end of the button transmission component (208) and movably installed on the surface of the shell (204), wherein when the press switch (206) is pressed, the press switch (206) pushes the button transmission component (208) to activate the control circuit board (209) inside the shell (204).

4. The device of claim 3, further comprising: a one-way suction module (203) set on a surface of the control circuit board (209) and fixedly installed inside the shell (204), wherein a top end of the one-way suction module (203) is configured to be compatible with the suction tube (202), and the control circuit board (209) triggers the battery (210) to power the one-way suction module (203) and controls the one-way suction module (203) to suction outward unidirectionally.

5. The device of claim 1, wherein the suction tube (202) is fixed inside the electric suction mechanism (2);

one section of the suction tube (202) is inside an interior of the shell (204), and the other section of the suction tube (202) extends to an outside of the electric suction mechanism (2); and the suction tube (202) is attached to the face mask (1) when the oral support (201) is not installed.

6. The device of claim 1, wherein the wearing connection mechanism (3) further includes a support column (307), the support column (307) being movably installed inside the one of the two casings (301); and a rotating disk (305) is movably installed on a surface of the support column (307), and a mainspring is fixedly installed on the surface of the support column (307).

7. The device of claim 6, wherein one end of the mainspring is fixedly installed with a fixed column, the fixed column being fixedly installed on a surface of the rotating disk (305);

the fixed column is fixedly installed on the surface of the retractable band (302);

the surface of the retractable band (302) is movably connected with a stopper rod, the stopper rod being fixedly installed inside the one of the two casings (301); and one end of the retractable band (302) is fixedly installed with a limit rod.

* * * * *